(12) United States Patent
Sun

(10) Patent No.: US 12,194,049 B2
(45) Date of Patent: Jan. 14, 2025

(54) **COMPOSITION FOR TREATING CARBAPENEM ANTIBIOTIC-RESISTANT *ACINETOBACTER BAUMANNII* INFECTION**

(71) Applicant: Guangzhou Century Clinical Research Co., Ltd., Guangzhou (CN)

(72) Inventor: Tianyu Sun, Guangzhou (CN)

(73) Assignee: Guangzhou Century Clinical Research Co., Ltd., Guangzhou (CN)

( * ) Notice: Subject to any disclaimer, the term of this patent is extended or adjusted under 35 U.S.C. 154(b) by 800 days.

(21) Appl. No.: 17/436,296

(22) PCT Filed: Feb. 20, 2020

(86) PCT No.: PCT/CN2020/076032
§ 371 (c)(1),
(2) Date: Sep. 3, 2021

(87) PCT Pub. No.: WO2020/177546
PCT Pub. Date: Sep. 10, 2020

(65) Prior Publication Data
US 2022/0175790 A1    Jun. 9, 2022

(30) Foreign Application Priority Data

Mar. 5, 2019 (CN) .......................... 201910162554.4

(51) Int. Cl.
*A61K 31/54* (2006.01)
*A61K 31/43* (2006.01)
*A61K 31/546* (2006.01)
*A61P 31/04* (2006.01)

(52) U.S. Cl.
CPC ............ *A61K 31/546* (2013.01); *A61K 31/43* (2013.01); *A61P 31/04* (2018.01)

(58) Field of Classification Search
CPC .................................................... A61K 31/546
See application file for complete search history.

(56) References Cited

FOREIGN PATENT DOCUMENTS

| CN | 1214246 A | 4/1999 |
|----|-----------|--------|
| CN | 103826639 A | 5/2014 |
| WO | 2013/085152 A1 | 6/2013 |

OTHER PUBLICATIONS

International Search Report dated May 26, 2020 issued in corresponding PCT/CN2020/076032 application (2 pages).
English Translation of Written Opinion issued in corresponding PCT/CN2020/076032 application (2 pages).

*Primary Examiner* — Shawquia Jackson
(74) *Attorney, Agent, or Firm* — MILLEN, WHITE, ZELANO & BRANIGAN, P.C.; Ryan R. Pool

(57) ABSTRACT

The application of a sulbactam and ceftazidime composition in the preparation of a drug for treating a carbapenem-resistant antibiotic *Acinetobacter baumannii* infection, characterized in the following: by mass, the amount of ceftazidime used in the sulbactam and ceftazidime composition comprising 10% to 90% of the amount of sulbactam used.

13 Claims, 1 Drawing Sheet

COMPOSITION FOR TREATING CARBAPENEM ANTIBIOTIC-RESISTANT *ACINETOBACTER BAUMANNII* INFECTION

CROSS-REFERENCE TO RELATED APPLICATIONS

The present application is a national phase entry under 35 USC § 371 of International Application PCT/CN2020/076032, filed on Feb. 20, 2020, which claims the benefit of and priority to Chinese Patent Application No. 2019101625544, filed on Mar. 5, 2019, the entire disclosures of which are incorporated herein by reference.

TECHNICAL FIELD

The present invention relates to the field of medicine, and in particular to a method and a composition for treating diseases caused by *Acinetobacter baumannii* infections, especially by carbapenem antibiotic-resistant *Acinetobacter baumannii* infections.

BACKGROUND ART

*Acinetobacter baumannii* is a non-fermenting Gram-negative bacterium and is an important pathogen. It is widely recognized that *Acinetobacter baumannii* is an important cause of serious infections. Clinically, serious infections in systems such as respiratory, blood, abdominal cavity, central nervous system, urinary and skin soft tissues are closely related to *Acinetobacter baumannii*.

Xiangxin L I et al. (Chinese Journal of Antibiotics, 2007, 32(12): 762-764) retrospectively investigated the clinical distribution of clinically isolated *Acinetobacter baumannii* from January 2002 to December 2006, and found that among 865 strains of *Acinetobacter baumannii* isolated within the 5 years, 75.7% were mainly derived from respiratory tract specimens. Chengdong S U N et al. (Chinese Critical Care Medicine, 2013, 25(6): 369-372) collected various microbial test specimens from inpatients in Beijing Jishuitan Hospital from January 2009 to December 2012 and isolated totally 307 strains of pandrug-resistant *Acinetobacter baumannii* in 4 years, which were originated mainly from respiratory tract secretions (69.4%) and secondly from wound surface secretions (14.7%), wherein the detection rates in the intensive care unit (ICU, 26.4%), respiratory department (26.1%), and geriatric department (23.1%) were the highest. Yili L I U et al. (International Journal of Laboratory Medicine, 2015(13): 1899-1901) carried out retrospective statistical analysis on the specimen source, ward distribution and drug-resistance evolution of 1678 strains of *Acinetobacter baumannii* isolated in Pudong Hospital Affiliated to Fudan University from January 2010 to October 2014, and the results showed that the clinically isolated *Acinetobacter baumannii* was mainly originated from respiratory tract specimens (79.1%), and the ward distribution was mainly in the intensive care unit (21.1%), neurosurgery department (17.7%) and cardiology department (17.6%).

A variety of antimicrobial drugs have varying degrees of antimicrobial activities against *Acinetobacter baumannii*, and each has its own advantages and disadvantages. Examples include antibiotics of cephalosporins, quinolones, sulbactam and sulbactam-containing compound preparations, carbapenems, colistins, glycylcyclines, and aminoglycoside, etc. Among them, colistins have the best antimicrobial effect against *Acinetobacter baumannii*; however, the tolerance is relatively poor. The hepatic and renal toxicity of glycylcyclines, aminoglycosides etc. is relatively high. Quinolones have a disabling risk. High adverse reactions often limit the clinical application of drugs. Cephalosporins have a relatively good safety. For example, the third-generation cephalosporin, ceftazidime has a relatively good antimicrobial effect on Gram-negative bacteria, especially possessing the best effect against *Pseudomonas aeruginosa*; however, its antimicrobial effect on *Acinetobacter baumannii* is moderate. Sulbactam also has a relatively good safety; however, sulbactam has always been used as a β-lactamase inhibitor in combination with other β-lactam antibiotics to improve the antimicrobial activity of the antibiotics, and representative sulbactam-containing compound preparations include ampicillin/sulbactam, cefoperazone/sulbactam etc.; furthermore, sulbactam itself has only a moderate degree of activity against *Acinetobacter baumannii*. Carbapenem antibiotics, such as imipenem, meropenem, panipenem, biapenem and doripenem, are very stable against β-lactamases and have strong antimicrobial effects, among which imipenem and meropenem are representatives; however, they are not as safe as cephalosporins and are strictly controlled in clinical use.

In recent years, the resistance of *Acinetobacter baumannii* to antimicrobial drugs has become increasingly serious.

For example, Xiangxin L I et al. as mentioned above found that the resistance of *Acinetobacter baumannii* clinically isolated from January 2002 to December 2006 to commonly used antimicrobial drugs increased year by year; Chengdong S U N et al. as mentioned above found that the resistance rate of *Acinetobacter baumannii* clinically isolated from the inpatients in Beijing Jishuitan Hospital from January 2009 to December 2012 to cefotaxime, piperacillin, meropenem, imipenem, ciprofloxacin, tetracycline etc. could be up to 100%; and Yili L I U et al. as mentioned above found that the 1678 strains of *Acinetobacter baumannii* isolated in Pudong Hospital affiliated to Fudan University from January 2010 to October 2014 were highly resistant to the first-generation and second-generation cephalosporins, cephamycins, ampicillin and nitrofurantoin, with the resistance rate reaching 90% or higher. The resistance rate to carbapenem antimicrobials, aztreonam, cefoperazone/sulbactam, and ampicillin/sulbactam also showed a significantly increasing trend. China Antimicrobial Surveillance Network (http://www.sific.com.cn/InsidePage/1000/67/7970.html) found in 2017 that clinically isolated *Acinetobacter baumannii* had a resistance rate of up to 72% to ceftazidime, up to 62.1% to ampicillin/sulbactam, up to 66.7% to imipenem, up to 69.3% to meropenem, and up to 43.5% to cefoperazone/sulbactam. According to the ranking of top 12 drug-resistant bacteria published by the World Health Organization in 2017, *Acinetobacter baumannii* was ranked No. 1 in the term of severe drug resistance level.

Sulbactam-related preparations have attracted attention in the treatment of drug-resistant *Acinetobacter baumannii* infections due to the better safety. Sulbactam itself has a relatively high MIC value for *Acinetobacter baumannii* and a limited antimicrobial effect. The synergistic effect of sulbactam-containing compound preparations on drug-resistant *Acinetobacter baumannii* has been studied.

Hua T A N et al. (Chinese Journal of Antibiotics, 2006, 31(8): 488-491) studied the effect of sulbactam combinations on cephalosporin-resistant *Acinetobacter baumannii*, wherein clinically isolated 56 strains of *Acinetobacter baumannii* resistant or intermediate to cefoperazone (CPZ), ceftazidime (CAZ) or cefotaxime (CTX) were divided into three groups: Group A was resistant to two or more of the above-mentioned drugs, Group B was resistant to CPZ only, and Group C was intermediate to CPZ or CTX. The minimal inhibitory concentrations (MICs) of single sulbactam and sulbactam combined with the above-mentioned three third-generation cephalosporins, were detected respectively by broth microdilution method. It was found that none of the combinations of sulbactam and any drug of CPZ, CAZ or CTX at the concentration of susceptibility and resistance breakpoint could cause the MICs of the sulbactam combination to be lower than that of single sulbactam. It was concluded that the single sulbactam had antimicrobial activity against multi-drug resistant *Acinetobacter baumannii*; however, the susceptibility of these strains to the combination preparations may be mainly due to the microbicidal effect of sulbactam.

Yishan HUANG et al. (China Practical Medicine, 2009, 4(31): 34-35) found that the application of sulbactam combined with third-generation cephalosporins could effectively reduce the MIC value of the third-generation cephalosporins against multi-drug resistant *Acinetobacter baumannii*, and for strains resistant to third-generation cephalosporins, the combination preparation could reduce the MIC to a susceptible range in case of a certain drug concentration being reached. However, from the data in the article, it can be seen that for imipenem-resistant *Acinetobacter baumannii* in Group C, although the use of sulbactam combined with ceftazidime reduced the MIC value of ceftazidime, without reducing the value to a susceptible range (according to CLSI standards, the MIC value of ceftazidime susceptible to *Acinetobacter baumannii* is ≤8 μg/ml), indicating that the clinical effect of the combined use of the two substances is not good.

Menglan ZHOU et al. (Chinese Journal of Clinical Laboratory Science, 2018, 36(1): 22-24) selected 23 strains of clinically meropenem-resistant *Acinetobacter baumannii* and 21 strains of meropenem-susceptible *Acinetobacter baumannii*, carried out a combined drug susceptibility test by the checkerboard dilution method, and calculated the fractional inhibitory concentration index (FIC) to determine the effect of combinations (synergy, partial synergy, irrelevance or antagonism). The results showed that the antimicrobial effect of the combined application of cefoperazone, tigecycline and sulbactam on *Acinetobacter baumannii* was mainly synergistic; the antimicrobial effect of the combined application of imipenem, colistin and sulbactam on *Acinetobacter baumannii* was mainly manifested as synergy and partial synergy; and the combined application of ceftazidime and sulbactam was mainly manifested as an irrelevant effect. From the data in the article, it can be seen that for meropenem-resistant *Acinetobacter baumannii* MRAB, cephalosporins combined with sulbactam did not show a synergistic effect, while cefoperazone combined with sulbactam mainly showed an additive effect (43.5%), and ceftazidime combined with sulbactam mainly showed an irrelevant effect (52.2%).

The resistance mechanisms of bacteria are quite complicated, and there are differences among different bacteria. The resistance mechanisms of *Acinetobacter baumannii* mainly include: (1) production of enzymes which inactivate antimicrobial drugs, including: 1) β-lactamases: TEM-type and SHY-type enzymes of class A, metallo-β-lactamases of class B, AmpC-type enzymes of class C, OXA-type enzymes of class D, etc.; and 2) aminoglycoside modifying enzymes; (2) changes in target sites of drug action: topoisomerases, 16S rRNA methylase gene mutations, etc.; and (3) decrease in the amount of drugs reaching the target sites of action, including a decrease in the permeability of outer membrane porin and the overexpression of efflux pumps.

The genome of *Acinetobacter baumannii* has shown that it is rich in efflux pump genes, and the high expression of efflux pumps plays an important role in the multi-drug resistance of *Acinetobacter baumannii*. (Qiuping L I U et al., Chinese Journal of Antibiotics, 2018, 43(10): 1179-1187)

The resistance of *Acinetobacter baumannii* to cephalosporins is mainly due to the production of large amounts of AmpC cephalosporinases. Since carbapenem antibiotics are highly stable against AmpC-type enzymes, clinically, carbapenem antibiotics are generally used for the treatment of cephalosporin-resistant *Acinetobacter baumannii* infection. However, for carbapenem-resistant *Acinetobacter baumannii*, the resistance mechanism is different, which is mainly attributed to production of OXA-type carbapenemases, in addition, down-regulation of membrane channel protein expression, over-expression of drug efflux pump, etc. also play important roles. Therefore, for *Acinetobacter baumannii* infections with different drug resistances, targeted treatment is required. However, for carbapenem antibiotic-resistant *Acinetobacter baumannii* infections, effective antibiotic compositions are lacking currently.

SUMMARY OF THE INVENTION

An object of the present invention is to provide the use of a composition of sulbactam and ceftazidime in the preparation of a medicament for treating the infection with carbapenem antibiotic-resistant *Acinetobacter baumannii*.

Another object of the present invention is to provide a method for treating the infection with carbapenem antibiotic-resistant *Acinetobacter baumannii*.

A further object of the present invention is to provide a composition of sulbactam and ceftazidime for treating the infection with carbapenem antibiotic-resistant *Acinetobacter baumannii*.

The technical solutions used by the present invention are as follows:

Use of a composition of sulbactam and ceftazidime in the preparation of a medicament for treating the infection with carbapenem antibiotic-resistant *Acinetobacter baumannii*, wherein the amount of ceftazidime in the sulbactam and ceftazidime composition is 10%-90% by mass of the amount of sulbactam.

In some embodiments, the amount of ceftazidime in the sulbactam and ceftazidime composition is 20%-80% of the amount of sulbactam.

In some embodiments, the amount of ceftazidime in the sulbactam and ceftazidime composition is 20%-40% of the amount of sulbactam.

In some embodiments, the amount of ceftazidime in the sulbactam and ceftazidime composition is 10%, 20%, 30%, 40%, 50%, 60%, 70%, 80% or 90% of the amount of sulbactam.

In some embodiments, the carbapenem antibiotic is at least one of meropenem, imipenem, panipenem, biapenem or doripenem.

In some embodiments, the carbapenem antibiotic-resistant *Acinetobacter baumannii* is also resistant to ceftazidime.

In some embodiments, the sulbactam and ceftazidime composition is a non-oral preparation.

In some embodiments, the sulbactam and ceftazidime composition is an injection or an inhalant.

In some embodiments, sulbactam and ceftazidime in the sulbactam and ceftazidime composition may be individually packaged (that is, the two are packaged separately and then combined), or may also be mixed packaged (that is, the two are mixed and then packaged). The two may be used in the form of a compound preparation after being mixed, or may also be used in combination in the form of single preparations.

In some embodiments, the daily dose of sulbactam in the sulbactam and ceftazidime composition is 2 g-20 g. It can be administered 2 to 4 times a day in divided doses.

In some embodiments, the daily dose of ceftazidime in the sulbactam and ceftazidime composition is 0.2 g-18 g. It can be administered 2 to 4 times a day in divided doses.

A method for treating the infection with carbapenem antibiotic-resistant *Acinetobacter baumannii* is provided, comprising administering to a patient therapeutically effective amounts of sulbactam and ceftazidime, wherein the amount of ceftazidime is 10%-90%, 20%-80% or 20%-40% by mass of the amount of sulbactam.

In some embodiments, the amount of ceftazidime is 10%, 20%, 30%, 40%, 50%, 60%, 70%, 80% or 90% of the amount of sulbactam.

In some embodiments, the carbapenem antibiotic-resistant *Acinetobacter baumannii* is resistant to at least one carbapenem antibiotic of meropenem, imipenem, panipenem, biapenem or doripenem.

In some embodiments, *Acinetobacter baumannii* is also resistant to ceftazidime.

In some embodiments, sulbactam and ceftazidime are used in the form of a compound preparation.

In some embodiments, sulbactam and ceftazidime are used in combination in the form of single preparations.

In some embodiments, the administration route is non-oral administration, preferably injection administration or inhalation administration.

The dose of administration may be adjusted according to the clinical severity of the disease. In some embodiments, the daily dose of sulbactam may be 2 g-20 g, and the daily dose of ceftazidime may be 0.2 g-18 g. It can be administered 2 to 4 times a day in divided doses.

A composition of sulbactam and ceftazidime for treating the carbapenem antibiotic-resistant *Acinetobacter baumannii* infection is provided, wherein the amount of ceftazidime in the sulbactam and ceftazidime composition is 10%-90%, 20%-80% or 20%-40% by mass of the amount of sulbactam.

In some embodiments, the carbapenem antibiotic-resistant *Acinetobacter baumannii* is resistant to at least one carbapenem antibiotic of meropenem, imipenem, panipenem, biapenem or doripenem.

In some embodiments, *Acinetobacter baumannii* is also resistant to ceftazidime.

In some embodiments, sulbactam and ceftazidime are packaged individually or in a mixed manner.

In some embodiments, the sulbactam and ceftazidime composition is a non-oral preparation. Furthermore, it is an injection or an inhalant.

Beneficial Effects of the Invention

In some embodiments, the sulbactam and ceftazidime composition can unexpectedly effectively treat the infections with carbapenem antibiotic-resistant *Acinetobacter baumannii*, and the therapeutic effect is even superior than that of a composition of carbapenem antibiotics and sulbactam.

DETAILED DESCRIPTION

Figure 1:
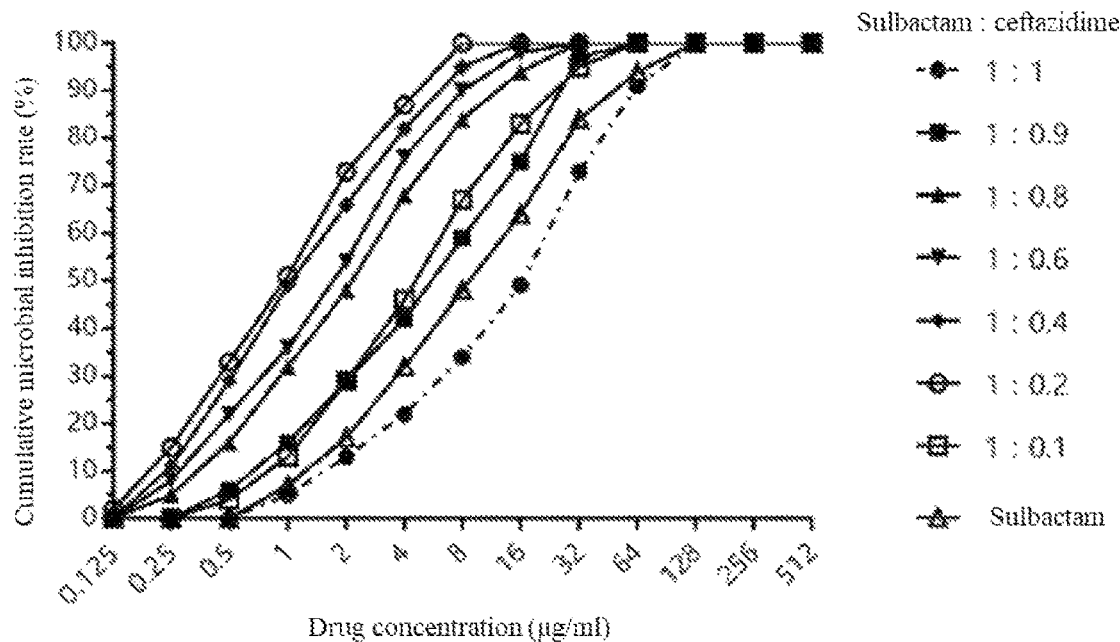
FIG. 1 shows the in vitro cumulative microbial inhibition rate of combinations of sulbactam and low-proportion ceftazidime against carbapenem antibiotic-resistant *Acinetobacter baumannii*.

The present invention will be described in detail below with specific embodiments. It should be understood that the content of the DETAILED DESCRIPTION section is illustrative rather than restrictive, that is, it does not impose any restriction on the content of the present invention.

Definition

The term "ceftazidime" refers to (6R,7R)-7-[[(2Z)-2-(2-Aminothiazol-4-yl)-2-[(1-carboxy-1-methylethoxy)imino]acetyl]amino]-8-oxo-3-[(1-pyridinio)methyl]-5-thia-1-azabicyclo[4.2.0]oct-2-ene-2-carboxylate, or its hydrates, solvates, polymorphs and/or pharmaceutical salts thereof. Examples include ceftazidime pentahydrate, ceftazidime sodium, etc. The amount described in the present invention is calculated based on (6R,7R)-7-[[(2Z)-2-(2-aminothiazol-4-yl)-2-[(1-carboxy-1-methylethoxy)imino]acetyl]amino]-8-oxo-3-[(1-pyridiniolmethyl]-5-thia-1-azabicyclo[4.2.0]oct-2-ene-2-carboxylate.

The term "sulbactam" refers to (2S,5R)-3,3-dimethyl-7-oxo-4-thia-1-azabicyclo[3.2.0]heptane-2-carboxylate-4,4-dioxide, or its hydrates, solvates, polymorphs and/or pharmaceutical salts thereof. Examples include sulbactam sodium, etc. The amount described in the present invention is calculated based on (2S,5R)-3,3-dimethyl-7-oxo-4-thia-1-azabicyclo[3.2.0]heptane-2-carboxylate-4,4-dioxide.

The "composition of sulbactam and ceftazidime" of the present invention may contain pharmaceutically applicable excipients according to the dosage form.

The term "CLSI" refers to the Clinical & Laboratory Standards Institute. Various publications published by CLSI are well known in the art. For example, CLSI-M100 is Performance Standards for Antimicrobial Susceptibility Tests. CLSI-M02 is Performance Standards for Antimicrobial Disk Susceptibility Tests. CLSI-M07 is Methods for Dilution Antimicrobial Susceptibility Tests for Bacteria that Grow Aerobically. CLSI also regularly revises the documents published. A person skilled in the art would be aware that the latest CLSI documents have the greatest reference value.

The term "MIC", i.e. the minimal inhibitory concentration, refers to the lowest concentration at which a drug can prevents the visible growth of bacteria (the bacteria are cultured at 37° C. for 24 h).

The term "resistant" in the expression "resistant *Acinetobacter baumannii*" means that according to the CLSI method (disk method or dilution method), *Acinetobacter baumannii* is tested with a drug, and the result is interpreted as resistance according to the CLSI-M100 standard.

Example 1: In Vitro Microbial Inhibition Effect of Combinations of Sulbactam and Low-Proportion Ceftazidime Against Drug-Resistant *Acinetobacter baumannii*

Strains: 157 clinically isolated strains of carbapenem antibiotic-resistant *Acinetobacter baumannii* were selected and named as CR-Ab. Selection criteria: The clinically isolated *Acinetobacter baumannii* was subjected to susceptibility testing using imipenem and meropenem (the commonly used representatives of carbapenems) according to the CLSI disk method, and the inclusion criteria was that the result of the susceptibility test showed resistance to one or both of meropenem or imipenem. Resistance refers to the MIC of imipenem and/or meropenem ≥8 µg/ml according to the criteria of Table 2B-2 of CLSI-M100 27th edition.

Drugs: Sulbactam and ceftazidime were taken and prepared into compositions of different ratios. The method was fixing the amount of sulbactam and gradually reducing the amount of ceftazidime to obtain compositions of sulbactam and ceftazidime at weight ratios of 1:1, 1:0.9, 1:0.8, 1:0.6, 1:0.4, 1:0.2 and 1:0.1, respectively. A sulbactam-only preparation was additionally used as a control.

Method: According to the CLSI broth microdilution method (the drug dilution concentration was 0.125-512 µg/ml), 157 strains of CR-Ab were subjected to susceptibility testing, and the MIC value of each composition was determined (the MIC value of sulbactam in the composition as the representative). The cumulative microbial inhibition rate was used to evaluate the microbial inhibition effects of the drugs, respectively. The cumulative microbial inhibition rate was defined as the microbial inhibition rate of a drug at a certain concentration plus all the microbial inhibition rates below that concentration. The microbial inhibition rate of a drug at a certain concentration=(the number of strains whose growth was inhibited at that drug concentration÷the total number of strains)×100%. The lower the drug concentration and the higher the cumulative microbial inhibition rate, the better the microbial inhibition effects.

Results: The cumulative microbial inhibition rate of each composition against carbapenem-resistant *Acinetobacter baumannii* CR-Ab was shown in Table 1, and taking the drug concentration as the abscissa and the cumulative microbial inhibition rate as the ordinate, concentration-cumulative microbial inhibition rate curves were plotted, as shown in FIG. 1.

0.2) showed superior effects. The results showed that the low-proportion ceftazidime unexpectedly and significantly enhanced the antimicrobial effects of sulbactam against carbapenem-resistant *Acinetobacter baumannii*.

Example 2: In Vitro Long-Term Microbicidal Effects of Combinations of Sulbactam and Low-Proportion Ceftazidime Against Drug-Resistant *Acinetobacter baumannii*

Strains: The carbapenem antibiotic-resistant *Acinetobacter baumannii* CR-Ab in Example 1 was taken.

Drugs: The four compositions of sulbactam and ceftazidime prepared at ratios of 1:1, 1:0.8, 1:0.4 and 1:0.2 in Example 1 were taken.

Method: Five CR-Ab strains were selected and subjected to susceptibility testing using each of these compositions to obtain the respective MIC value thereof. Subsequently, bacterial suspension with a concentration of $10^6$ CFU/mL obtained after culturing the strain with an MH broth (Mueller-Hinton broth) was used as an inoculum. The inoculum was taken separately, each drug composition was added such that the final concentrations of the drug (based on the sulbactam concentration) were respectively 0 (negative control), 0.25 MIC, 1 MIC, 2 MIC, 4 MIC, 8 MIC and 16 MIC. Samples were respectively taken at the time points of 0, 2 h, 4 h, 6 h, 8 h, 12 h and 24 h, diluted by 10 times, and then inoculated on agar plates. The agar plates were placed in an incubator at 37° C. and cultured for 24 hours, followed by bacterial counting, and the data of the five strains were averaged and then analyzed as one datum. The difference of the bacterial counts log 10 CFU per ml between before and after administration (Δ log 10 CFU/ml) indicated the strength of microbicidal activity. Δ log 10 CFU/ml was defined as the bacterial log 10 CFU/ml after administration minus the bacterial log 10 CFU/ml before administration. At

TABLE 1

Cumulative microbial inhibition rates (%) of sulbactam:ceftazidime at different ratios against CR-Ab

| Drug concentration (sulbactam, µg/ml) | Compositions with different ratios (sulbactam:ceftazidime) | | | | | | | Single sulbactam |
|---|---|---|---|---|---|---|---|---|
| | 1:1 | 1:0.9 | 1:0.8 | 1:0.6 | 1:0.4 | 1:0.2 | 1:0.1 | |
| 0.125 | 0 | 0 | 0 | 0 | 0 | 2 | 0 | 0 |
| 0.25 | 0 | 0 | 5 | 8 | 11 | 15 | 0 | 0 |
| 0.5 | 0 | 6 | 16 | 22 | 29 | 33 | 4 | 0 |
| 1 | 5 | 16 | 32 | 36 | 49 | 51 | 13 | 7 |
| 2 | 13 | 29 | 48 | 54 | 66 | 73 | 29 | 17 |
| 4 | 22 | 42 | 68 | 76 | 82 | 87 | 46 | 32 |
| 8 | 34 | 59 | 84 | 90 | 95 | 100 | 67 | 48 |
| 16 | 49 | 75 | 94 | 98 | 100 | 100 | 83 | 64 |
| 32 | 73 | 97 | 100 | 100 | 100 | 100 | 95 | 84 |
| 64 | 91 | 100 | 100 | 100 | 100 | 100 | 100 | 94 |
| 128 | 100 | 100 | 100 | 100 | 100 | 100 | 100 | 100 |
| 256 | 100 | 100 | 100 | 100 | 100 | 100 | 100 | 100 |
| 512 | 100 | 100 | 100 | 100 | 100 | 100 | 100 | 100 |

It could be seen from Table 1 and FIG. 1 that compositions of sulbactam and low-proportion ceftazidime showed better effects against carbapenem-resistant *Acinetobacter baumannii*. Compared with the 1:1 composition of sulbactam and ceftazidime or the sulbactam-only preparation, the concentration-cumulative microbial inhibition rate curves of the compositions of sulbactam and low-proportion ceftazidime shifted significantly to the left, indicating that the microbial inhibition effects were significantly enhanced. In particular, the compositions in the ratio range of 1:(0.8- the same sampling time, the smaller the Δ log 10 CFU/ml, the better the microbicidal effect.

Figure 2:
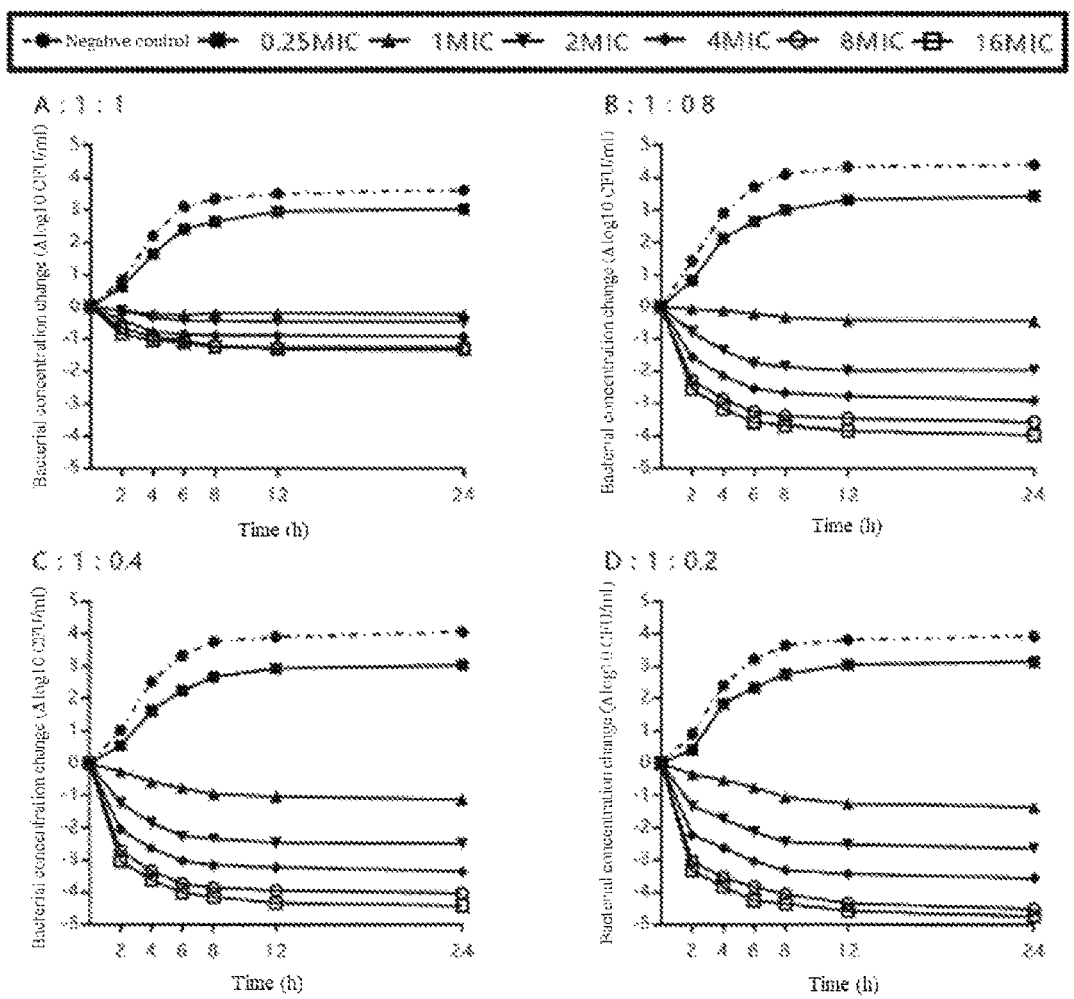
FIG. 2 shows the in vitro long-term microbicidal effects of combinations of sulbactam and low-proportion ceftazidime against carbapenem antibiotic-resistant *Acinetobacter baumannii*.

Results: Tables 2-5 listed the differences of the bacterial counts of CR-Ab between before and after the composition with each ratio was added. Taking the sampling time as the abscissa and the difference of the bacterial counts between before and after administration, Δ log 10 CFU/ml, as the ordinate, time-microbicidal curves were plotted, as shown in FIG. 2 (A was 1:1 sulbactam and ceftazidime, B was 1:0.8 sulbactam and ceftazidime, C was 1:0.4 sulbactam and ceftazidime, and D was 1:0.2 sulbactam and ceftazidime). It could be seen from the results that compared with the 1:1 composition of sulbactam and ceftazidime, the long-term microbicidal effects of sulbactam and low-proportion ceftazidime (1:(0.8-0.2)) were significantly stronger, indicating there were unexpected effects.

TABLE 2

Difference of the bacterial counts of CR-Ab between before and after 1:1 sulbactam and ceftazidime was added ($\Delta$log10 CFU/ml)

| Sampling time (h) | Negative control | Drug concentration (sulbactam) | | | | | |
|---|---|---|---|---|---|---|---|
| | | 0.25MIC | 1MIC | 2MIC | 4MIC | 8MIC | 16MIC |
| 0 | 0 | 0 | 0 | 0 | 0 | 0 | 0 |
| 2 | 0.82 | 0.62 | −0.11 | −0.13 | −0.42 | −0.65 | −0.84 |
| 4 | 2.21 | 1.64 | −0.23 | −0.32 | −0.78 | −0.93 | −1.04 |
| 6 | 3.11 | 2.42 | −0.24 | −0.43 | −0.85 | −1.04 | −1.12 |
| 8 | 3.35 | 2.65 | −0.21 | −0.44 | −0.88 | −1.22 | −1.24 |
| 12 | 3.52 | 2.96 | −0.2 | −0.46 | −0.88 | −1.25 | −1.31 |
| 24 | 3.63 | 3.04 | −0.23 | −0.47 | −0.92 | −1.25 | −1.32 |

TABLE 3

Difference of the bacterial counts of CR-Ab between before and after 1:0.8 sulbactam and ceftazidime was added ($\Delta$log10 CFU/ml)

| Sampling time (h) | Negative control | Drug concentration (sulbactam) | | | | | |
|---|---|---|---|---|---|---|---|
| | | 0.25MIC | 1MIC | 2MIC | 4MIC | 8MIC | 16MIC |
| 0 | 0 | 0 | 0 | 0 | 0 | 0 | 0 |
| 2 | 1.43 | 0.82 | −0.07 | −0.77 | −1.56 | −2.27 | −2.55 |
| 4 | 2.91 | 2.13 | −0.11 | −1.35 | −2.13 | −2.86 | −3.16 |
| 6 | 3.72 | 2.64 | −0.21 | −1.74 | −2.55 | −3.25 | −3.57 |
| 8 | 4.12 | 3.01 | −0.33 | −1.86 | −2.67 | −3.38 | −3.66 |
| 12 | 4.35 | 3.33 | −0.42 | −1.98 | −2.77 | −3.46 | −3.83 |
| 24 | 4.41 | 3.44 | −0.44 | −1.97 | −2.91 | −3.57 | −3.96 |

TABLE 4

Difference of the bacterial counts of CR-Ab between before and after 1:0.4 sulbactam and ceftazidime was added ($\Delta$log10 CFU/ml)

| Sampling time (h) | Negative control | Drug concentration (sulbactam) | | | | | |
|---|---|---|---|---|---|---|---|
| | | 0.25MIC | 1MIC | 2MIC | 4MIC | 8MIC | 16MIC |
| 0 | 0 | 0 | 0 | 0 | 0 | 0 | 0 |
| 2 | 1.03 | 0.55 | −0.24 | −1.23 | −2.05 | −2.71 | −3.03 |
| 4 | 2.52 | 1.63 | −0.56 | −1.84 | −2.63 | −3.34 | −3.61 |
| 6 | 3.33 | 2.25 | −0.77 | −2.25 | −3.02 | −3.73 | −4.01 |
| 8 | 3.76 | 2.66 | −0.95 | −2.33 | −3.15 | −3.85 | −4.14 |
| 12 | 3.91 | 2.93 | −1.03 | −2.46 | −3.22 | −3.94 | −4.33 |
| 24 | 4.06 | 3.03 | −1.12 | −2.48 | −3.35 | −4.03 | −4.42 |

TABLE 5

Difference of the bacterial counts of CR-Ab between before and after 1:0.2 sulbactam and ceftazidime was added ($\Delta$log10 CFU/ml)

| Sampling time (h) | Negative control | Drug concentration (sulbactam) | | | | | |
|---|---|---|---|---|---|---|---|
| | | 0.25MIC | 1MIC | 2MIC | 4MIC | 8MIC | 16MIC |
| 0 | 0 | 0 | 0 | 0 | 0 | 0 | 0 |
| 2 | 0.91 | 0.43 | −0.34 | −1.32 | −2.21 | −3.03 | −3.33 |
| 4 | 2.42 | 1.84 | −0.52 | −1.73 | −2.63 | −3.54 | −3.82 |

TABLE 5-continued

Difference of the bacterial counts of CR-Ab between before and after 1:0.2 sulbactam and ceftazidime was added ($\Delta$log10 CFU/ml)

| Sampling time (h) | Negative control | Drug concentration (sulbactam) | | | | | |
|---|---|---|---|---|---|---|---|
| | | 0.25MIC | 1MIC | 2MIC | 4MIC | 8MIC | 16MIC |
| 6 | 3.22 | 2.34 | −0.74 | −2.12 | −3.03 | −3.83 | −4.25 |
| 8 | 3.64 | 2.76 | −1.05 | −2.44 | −3.32 | −4.06 | −4.36 |
| 12 | 3.82 | 3.05 | −1.24 | −2.51 | −3.43 | −4.34 | −4.57 |
| 24 | 3.93 | 3.14 | −1.36 | −2.64 | −3.57 | −4.52 | −4.74 |

It could be seen from the results that compared with the 1:1 composition of sulbactam and ceftazidime, the long-term microbicidal effects of sulbactam and low-proportion ceftazidime (1:(0.2-0.8)) were significantly superior, indicating there were unexpected effects.

Example 3: Protective Effects of Combinations of Sulbactam and Low-Proportion Ceftazidime in Pneumonia Model Animals Infected with Drug-Resistant *Acinetobacter baumannii*

Drugs: The compositions of sulbactam and ceftazidime at ratios of 1:1, 1:0.9, 1:0.8, 1:0.6, 1:0.4, 1:0.2 and 1:0.1, as used in Example 1, were prepared into drug solutions with water for injection; commercially available meropenem was prepared into drug solutions with water for injection; and commercially available meropenem plus sulbactam was prepared into 1:1 drug solutions of meropenem and sulbactam with water for injection.

Strains: CR-Ab strains were used and cultured into a bacterial suspension with a concentration of $10^8$ CFU/mL.

Animals: Male C57BL/6 mice were randomly divided into a normal control group, a model control group, a meropenem group, a 1:1 meropenem and sulbactam group, a 1:1 sulbactam and ceftazidime group, a 1:0.9 sulbactam and ceftazidime group, a 1:0.8 sulbactam and ceftazidime group, a 1:0.6 sulbactam and ceftazidime group, a 1:0.4 sulbactam and ceftazidime group, a 1:0.2 sulbactam and ceftazidime group and a 1:0.1 sulbactam and ceftazidime group. Each group was divided into two subgroups, low-dose and high-dose, and each subgroup was assigned 15 animals.

Test method: Except the normal control group, the mice in each group were intraperitoneally injected with 50 mg/kg of cyclophosphamide, and further intraperitoneally injected with 50 mg/kg of cyclophosphamide after 3 days. Then, 1 day later, except the normal control group, the mice in each group were respectively injected with 80 μL of the bacterial suspension through the airway, and the mice in the normal control group were injected with the same amount of normal saline. Starting from 1 day before the injection of the bacterial suspension, the mice in each group, except the normal control group and the model control group, were respectively intraperitoneally injected with a low dose (10 mg/kg) and a high dose (30 mg/kg) of the drug for each group, and the mice in the normal control group and the model control group were injected with the same amount of normal saline. The administration frequency was once a day. After 7 days, the number of surviving mice was counted.

Results: Table 6 listed the main results of the test. Cyclophosphamide is an immunosuppressant, the injection of which led to that the immunity of mice was reduced and the mice were more susceptible to CR-Ab infection. The mice in each group showed obvious shortness of breath, decreased activity, and slow response during the test period. Almost all mice in the model control group died after 7 days. Autopsy of the dead mice revealed severe inflammatory changes in the lungs, including typical pneumonia pathological changes such as bronchial wall thickening, bronchiectasis, monocyte exudation, and severe pulmonary interstitial congestion, indicating that the modeling was successful. From the survival of the mice in each group after 7 days, it could be seen that the compositions of sulbactam and low-proportion ceftazidime (1:(0.2-0.8)) could better protect infected mice, the effect of which was significantly better than that of the 1:1 composition of sulbactam and ceftazidime, and even superior to that of the composition of carbapenem and sulbactam.

TABLE 6

Survival of CR-Ab pneumonia model mice (survival number/total number)

| Group | Low dose | High dose |
|---|---|---|
| Normal control group | 15/15 | 14/15 |
| Model control group | 1/15 | 0/15 |
| Meropenem group | 2/15 | 3/15 |
| 1:1 meropenem and sulbactam group | 8/15 | 9/15 |
| 1:1 sulbactam and ceftazidime group | 4/15 | 5/15 |
| 1:0.9 sulbactam and ceftazidime group | 9/15 | 9/15 |
| 1:0.8 sulbactam and ceftazidime group | 12/15 | 14/15 |
| 1:0.6 sulbactam and ceftazidime group | 12/15 | 15/15 |
| 1:0.4 sulbactam and ceftazidime group | 13/15 | 15/15 |
| 1:0.2 sulbactam and ceftazidime group | 14/15 | 15/15 |
| 1:0.1 sulbactam and ceftazidime group | 10/15 | 10/15 |

Possible Mechanisms of Action

On the one hand, sulbactam could inhibit 0-lactamases to overcome bacterial resistance, and on the other hand, it could also exert the antibacterial effect by binding to penicillin-binding proteins (PBPs) of *Acinetobacter baumannii*. This dual effect had certain advantages. However, the effect of using sulbactam alone was not good. Carbapenem antibiotic-resistant *Acinetobacter baumannii* (CR-Ab) was generally highly resistant to ceftazidime, and the use of ceftazidime alone also made little sense.

The above-mentioned experimental data indicated that the use of sulbactam and ceftazidime in combination at a specific ratio had an excellent therapeutic effect on CR-Ab infection, and the therapeutic effect thereof was even stronger than that of the composition of carbapenem and sulbactam. The possible reasons were as follows: on the one hand, since CR-Ab was highly resistant to ceftazidime, and the 0-lactamases produced by CR-Ab had a strong affinity for ceftazidime, so the addition of ceftazidime could protect sulbactam from being hydrolyzed by the 0-lactamases to some extent; furthermore, ceftazidime could also reduce the chance of sulbactam being effluxed by occupying drug efflux pumps. On the other hand, since sulbactam needed to bind to the PBPs of *Acinetobacter baumannii* to exert the antimicrobial effect, and the affinity of ceftazidime to the PBPs was greater than that of sulbactam, thus the occupation of the PBP targets by too much ceftazidime was not conducive to the antimicrobial effect of sulbactam. Therefore, the amount of ceftazidime needed to be controlled within a certain proportion range.

Although the present invention has been described in detail hereinabove with general descriptions and specific embodiments, some modifications or improvements can be made on the basis of the present invention, which would be obvious to a person skilled in the art. Therefore, these modifications or improvements made on the basis of the present invention and not departing from the spirit thereof still fall within the scope of the present invention.

The invention claimed is:

1. A method of treating infection with carbapenem antibiotic-resistant *Acinetobacter baumannii*, comprising: administering a therapeutically effective amount of a composition comprising sulbactam and ceftazidime to a subject in need thereof, wherein the amount of ceftazidime in the composition of sulbactam and ceftazidime is 10%-90% by mass of the amount of sulbactam.

2. The method according to claim 1, wherein the amount of ceftazidime is 20%-80% of the amount of sulbactam.

3. The method according to claim 1, wherein the amount of ceftazidime is 20%-40% of the amount of sulbactam.

4. The method according to claim 1, wherein the carbapenem antibiotic is at least one of meropenem, imipenem, panipenem, biapenem or doripenem.

5. The method according to claim 4, wherein the carbapenem antibiotic-resistant *Acinetobacter baumannii* is also resistant to ceftazidime.

6. The method according to claim 1, wherein the composition of sulbactam and ceftazidime is a non-oral preparation.

7. The method according to claim 6, wherein the composition of sulbactam and ceftazidime is an injection or an inhalant.

8. The method according to claim 1, wherein sulbactam and ceftazidime in the composition of sulbactam and ceftazidime are packaged individually or in a mixed manner.

9. The method according to claim 1, wherein the daily dose of sulbactam in the composition of sulbactam and ceftazidime is 2 g-20 g.

10. The method according to claim 1, wherein the daily dose of ceftazidime in the composition of sulbactam and ceftazidime is 0.2 g-18 g.

11. The method according to claim 2, wherein the carbapenem antibiotic is at least one of meropenem, imipenem, panipenem, biapenem or doripenem.

12. The method according to claim 11, wherein the carbapenem antibiotic-resistant *Acinetobacter baumannii* is also resistant to ceftazidime.

13. The method according to claim 9, wherein the daily dose of ceftazidime in the composition of sulbactam and ceftazidime is 0.2 g-18 g.

\* \* \* \* \*